United States Patent
Alexander et al.

(10) Patent No.: US 10,488,423 B2
(45) Date of Patent: Nov. 26, 2019

(54) METHOD

(71) Applicant: Mars, Incorporated, McLean, VA (US)

(72) Inventors: Janet Alexander, Waltham-on-the-Wolds (GB); Penelope Morris, Waltham-on-the-Wolds (GB); Adrian Hewson-Hughes, Waltham-on-the-Wolds (GB)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 15/381,834

(22) Filed: Dec. 16, 2016

(65) Prior Publication Data
US 2017/0176466 A1    Jun. 22, 2017

(30) Foreign Application Priority Data
Dec. 17, 2015    (GB) .................................. 1522296.1

(51) Int. Cl.
*G01N 33/74*    (2006.01)
*A23K 50/42*    (2016.01)
(Continued)

(52) U.S. Cl.
CPC ........... *G01N 33/74* (2013.01); *A23K 20/147* (2016.05); *A23K 20/158* (2016.05); *A23K 50/42* (2016.05); *A23K 50/48* (2016.05); *A61K 9/0056* (2013.01); *A61K 31/198* (2013.01); *A61K 31/20* (2013.01); *A61K 31/201* (2013.01); *A61K 31/202* (2013.01); *A61K 31/401* (2013.01); *G01N 2333/645* (2013.01)

(58) Field of Classification Search
None
See application file for complete search history.

(56) References Cited

U.S. PATENT DOCUMENTS

| 4,296,132 A | 10/1981 | Haas et al. |
| 4,868,001 A | 9/1989 | Maruta et al. |
| (Continued) | | |

FOREIGN PATENT DOCUMENTS

| CN | 106360028 A | 2/2017 |
| DE | 2947503 A1 | 5/1981 |
| (Continued) | | |

OTHER PUBLICATIONS

Smilla Light, Available from: ww.zooplus.com Jul. 8, 2015, https://web.archive.Org/web/20150708212250/http://www.zooplus.co.uk/shop/cats/supplements_specialty_cat_food/cat_diet_foods/dry_cat_diet_foods/221597, 3 pp.*

(Continued)

*Primary Examiner* — Karl J Puttlitz
(74) *Attorney, Agent, or Firm* — Mars, Incorporated

(57) ABSTRACT

A method is provided, comprising feeding a cat a foodstuff comprising a protein to fat ratio of 1:0.27 to 1:0.63 on a gram:gram as fed or dry matter basis, and measuring the level of glucose-dependent insulinotropic polypeptide (GIP) in a blood sample from the cat before and after feeding the foodstuff. A reduction in GIP levels and/or maintaining low levels of GIP post-prandially is indicative of a foodstuff useful in preventing accumulation of and/or reducing body fat in a cat and therefore controlling the body weight of a cat.

7 Claims, 3 Drawing Sheets

(51) Int. Cl.
| | |
|---|---|
| A61K 9/00 | (2006.01) |
| A61K 31/198 | (2006.01) |
| A61K 31/20 | (2006.01) |
| A61K 31/201 | (2006.01) |
| A61K 31/202 | (2006.01) |
| A61K 31/401 | (2006.01) |
| A23K 20/147 | (2016.01) |
| A23K 20/158 | (2016.01) |
| A23K 50/48 | (2016.01) |

(56) References Cited

U.S. PATENT DOCUMENTS

| | | | |
|---|---|---|---|
| 5,051,270 | A | 9/1991 | Ueda et al. |
| 5,141,755 | A | 8/1992 | Weisman |
| 5,422,352 | A | 6/1995 | Astrup |
| 5,643,622 | A | 7/1997 | Sawhill et al. |
| 5,775,913 | A | 7/1998 | Martin et al. |
| 5,776,887 | A | 7/1998 | Lee et al. |
| 5,780,039 | A | 7/1998 | Greenberg et al. |
| 5,804,210 | A | 9/1998 | Cook et al. |
| 5,855,917 | A | 1/1999 | Cook et al. |
| 5,900,248 | A | 5/1999 | Crane et al. |
| 5,932,258 | A | 8/1999 | Sunvold |
| 6,071,544 | A * | 6/2000 | Sunvold ............... A23K 20/147 426/2 |
| 6,203,825 | B1 | 3/2001 | Hodgkins |
| 6,238,708 | B1 | 5/2001 | Hayek et al. |
| 8,142,810 | B2 | 3/2012 | Sunvold |
| 2004/0161495 | A1 | 8/2004 | Sergheraert et al. |
| 2011/0178005 | A1 | 7/2011 | Yamka et al. |
| 2016/0136124 | A1 | 5/2016 | Franzen et al. |
| 2017/0112167 | A1 | 4/2017 | Cambou et al. |
| 2018/0295862 | A1 | 10/2018 | Mao et al. |
| 2018/0368446 | A1 | 12/2018 | Allaway et al. |

FOREIGN PATENT DOCUMENTS

| | | | |
|---|---|---|---|
| WO | 2010009478 | | 7/2009 |
| WO | 2010/009478 | * | 1/2010 |

OTHER PUBLICATIONS

Nasteska et al., Diabetes. Jul. 2014;63(7):2332-43.*
Dozier et al., Nutrient Compostion of Feed-Grade and Pet-Food-Grade Poultry By-Product Meal (2003) (Year: 2003).*
Aldrich, USA poultry meal: quality issues and concerns in pet foods, 2007, downloaded from the internet on Jun. 11, 2018 from https://en.engomix.com/feed-machinery/articles/poultry-meal-in-pet-foods-t33667.htm (Year: 2007).*
Physiology and Pharmacology of Diabetes Therapies in the Cat: Insulin Detemir, Insulin Glargine, Exenatide and the Incretin Effect by Chen Gilor, Dissertation, Veterinary Clinical Medicine in the Graduate College of the University of Illinois at Urbana-Champaign, 2010 (Year: 2010).*
"Hill's Science Plan Adult Cat Light Wet Food—Chicken", Available from www.zooplus.com, Aug. 3, 2014, from: https://web.archive.org/web/20140803092127/http://www.zooplus.co.uk/shop/cats/supplements_specialty_cat_food/cat_diet_foods/wet_cat_food/13485, 2 pp.
"Perfect Fit In-Home Pouches", www.zooplus.com, Aug. 3, 2014, available from: http://web.archive.org/web/20140803085402/http://www.zooplus.co.uk/shop/cats/supplements_specialty_cat_food/cat_diet_foods/wet_cat_food/41212, 2 pp.
"Royal Canin Indoor Cat", www.zooplus.co.uk, Jun. 26, 2015available from http://web.archive.org/web/20150626202640/http://www.zooplus.co.uk/shop/cats/dry_cat_food/royal_canin/royalcanin_health_nutrition/13470, 2 pp.
"Sanabelle Light", www.zooplus.co.uk, Jun. 13, 2015, available from http://web.archive.org/web/20150716075914/http://www.zooplus.co.uk./shop/cats/supplements_speciality_cat_food/cat_diet_foods/dry_cat_diet_foods_14535, 2 pp.
"Smilla Light", Available from: www.zooplus.com Jul. 8, 2015, https://web.archive.org/web/20150708212250/http://www.zooplus.co.uk/shop/cats/supplements_specialty_cat_food/cat_diet_foods/dry_cat_diet_foods/221597, 3 pp.
Chen, et al., "Increased GIP Signaling Induces Adipose Inflammation via a HIF-1a-dependent Pathway and Impairs Insulin Sensitivity in Mice", Am J Physiol Endocrinol Megab 308: p. E414-E425, 2015.
German, et al., "Imprecision when using Measuring Cups to Weigh out Extruded Dry Kibbled Food", Journal of Animal Physiology and Animal Nutrition, 95, 2011, pp. 368-373.
German, "The Growing Problem of Obesity in Dogs and Cats", Journal of Nutrition, Supplement, 2006, pp. 1940S-1946S.
Gogobakan, et al., "GIP Increases Adipose Tissue Expression and Blood Levels of MSP-1 in Humans and Links High Energy Diets to Inflammation: A Randomised Trial", Diabetologia, 2015, 58:1759-1768.
Hewson-Hughes, et al., "Geometric Analysis of Macronutrient Selection in the Adult Domestic Cat, *Felis catus*", Journal of Experimental Biology, 2011, 214, pp. 1039-1051, available from: http://jeb.biologists.org/content/214/6/1039.full.
Irwin, et al., "Evidence for Beneficial Effects of Compromised Gastric Inhibitory Polypeptide Action in Obesity-Related Diabetes and Possible Therapeutic Implications", Diabetologia (2009) 52: p. 1727-1731.
Lund, et al., "Prevalence and Risk Factors for Obesity in Adult Cats from Private US Veterinary Practices", Intern. J. Appl. Res. Vet. Med., vol. 3, No. 2, 2005, pp. 88-96.
McLean, et al., "GIP Receptor Antagonism Reverses Obesity, Insulin Resistance, and Associated Metabolic Dstrubances Induced in Mice by Prolonged Conusmption of High-Fat Dient", Am J Physiol Endocrinol Metab 293: pp. 6-E1755, 2007.
Anonymous, "Cat Food with Chicken for Adult Cats", Database GNPD MINTEL, May 2015, XP002768641, Database accession No. 3198779, 2 pgs.
Anonymous, "Wet Cat Food with Beef in Sauce", Database GNPD MINTEL, Jun. 2013, XP002768642, Database accession No. 2094479, 2 pgs.
McClean, et al., "GIP Receptor antagonism reverses obesity, insulin resistance, and associated metabolic distrubances induced in mice by prolonged consumption of high-fat diet", American Jounral of Physiology: Endocrinology and Metabolism, American Physiological Society, Bethesda, MD, US, vol. 293, No. 6, Jan. 1, 2007, p. E1746-1755, XP008099009.
Thomsen, et al., "Differential effects of saturated and monounsaturated fatty acids on postprandial lipemia and incretin responses in healthy subjects", The American Journal of Clinical Nutrition, Jan. 1, 1999, XP055358860, Retrieved from the internet: http://ajcn.nutrition.org/content/69/6/1135.full.pdf#page=1&view=FitH (retrieved on Mar. 27, 2017), 9 pgs.
R/d Feline Product Specification Page, Hills Pet Nutrition Inc., Apr. 15, 2008, 2 pgs.
"Food Energy Definition", Oct. 28, 2008, 4 pgs.
"Optimal Nutrition for Exercise and Good Health", Health 410, 2000, online, Chapter 10, 22 pages, downloaded Aug. 23, 2006.
Baba, et al., "High Protein vs. High Carbohydrate Hypoenergetic Diet for the Treatment of Obese Hyperinsulinemic Subjects", Int. J. Obes. Relat. Metab. Disord., Nov. 1999, 23(11), Abstract only.
Biourge, et al., "Effects of Protein, Lipid, or Carbohydrate Supplementation on Hepatic Lipid Accumulation during Rapid Weight Loss in Cats", Am. J. Vet. Res., vol. 55, No. 10, Oct. 1994, Abstract only.
Butchi Lakshmi, et al., "Hypoglycemic Effect of Selected Sorghum Recipes", Nutrition Research, 16(10), Jan. 1996, pp. 1651-1658.
Facchini, et al., "Insulin Resistance as a Predictor of Age-Related Diseases", The Journal of Clinical Endocrinology & Metabolism, Aug. 2001, 86(8): 3574-3578.
Foster-Powell, et al., "International Table of Glycemic Index and Glycemic Load Values", Am. J. Clin. Nutr., vol. 75 pp. 5-56, Jul. 2002.

(56) References Cited

OTHER PUBLICATIONS

Jones, et al., "Cutaneous Xanthomata Associated with Diabetes Mellitus in a Cat", Journal of Small Animal Practice, vol. 26, Jan. 1985, abstract only.

Kealy, et al., "Effects of Diet Restriction on Life Span and Age-Related Changes in Dogs", JAVMA, vol. 220, No. 9, May 1, 2002, 1315, 1317-1320.

Koyama, et al., "Tissue Triglycerides, Insulin Resistance and Insulin Production; Implications for Hyperinsulinemia of Obesity", Am. J. Physiol., Oct. 1997,E708-E712.

Lane, et al., "Calorie Restriction in Nonhuman Primates: Implications for Age-Related Disease Risk", Journal of Anti-Aging Medicine, vol. 1, No. 4, pp. 315-326, Dec. 1998.

Legro, et al., "A Fasting Glucose to Insulin Ratio is a Useful Measure of Insulin Sensitivity in Women with Polycystic Ovary Syndrome", J. Clin. Endocrine. Metab., Aug. 1998, 83(8), pp. 2694-2698.

Martin, et al., "Recommandations Nutritionnelles Dans Le Traitement Des Principales Affections du Chat", Point Veterinaire, Editions du Point Veterinaire, Maisons-Alfort, FR, vol. 28, No. 178, Aug. 1996, pp. 327-337.

Pawlosky, et al., "Essential Fatty Acid Metabolism in the Feline: Relationship between Liver and Brain Production of Long-Chain Polyunsaturated Fatty Acids", J. of Lipid Research, vol. 35, pp. 2032-2040, Nov. 1994.

Ramsey, et al., "Dietary Restriction and Aging in Rehesus Monkeys: The University of Wisconsin Study", Experimental Gerontology, 35 (Jun. 2000) 1131-1149.

Reaven, et al., "Effect of Age and Diet on Insulin Secretion and Insulin Action in the Rat", Diabetes, Feb. 1983, 32(2); 175-180, Abstract only.

Romsos, et al., "Effects of Dietary Carbohydrate, Fat and Protein on Growth, Body Composition and Blood Metabolite Levels in the Dog", J. Nutr., 106, Oct. 1976, pp. 1452-1464.

St. Jeor, et al., "Dietary Protein and Weight Reduction: A Statement for Healthcare Professionals from the Nutrition Committee of the Council on Nutrition, Physical Activity and Metabolism of the American Heart Association", Circulation. Oct. 2001;104:1869-1874.

Youngren, et al., "Impaired Insulin-Receptor Autophophorylationis an early Defect in Fat-Fed, Insulin-Resistant Rats", J. Appl. Physiol., 91:2240-2247, Nov. 2001.

Anon, "Scientific Opinion on the Safety and Efficacy of the Use of Amino Acids (chemical group 34) when used as Flavourings for all Animal Species", The EFSA Journal, vol. 12, No. 5:3670. 10 pages, May 1, 2014.

Beauchamp, et al., "Flavor Preferences in Cats (*Felis catus* and *Panthera* sp.)", Journal of Comparative and Physiological Psychology Apr. 1977, vol. 91, No. 5, 1118-1127.

* cited by examiner

METHOD

CROSS REFERENCE TO RELATED APPLICATIONS

This application claims the benefit of Great Britain Patent Application No. GB1522296.1, filed on Dec. 17, 2015 which is incorporated herein by reference in its entirety for any and all purposes.

FIELD

The present invention relates to methods of determining the levels of glucose-dependent insulinotropic polypeptide (GIP) before and after a meal in a companion animal, wherein the meal is a pet foodstuff having a particular protein to fat ratio, which is useful in reducing the levels of GIP and maintaining low levels of GIP post-prandially and having the beneficial effects as described herein.

BACKGROUND

The metabolic response to food intake is regulated by gastro-intestinal and other peptide hormones and energy intermediate metabolites. However, intake must be regulated to maintain certain plasma metabolites (e.g. glucose) within a safe physiological range. This complex balance is co-ordinated by the brain, and uses a variety of neural, hormonal and metabolite signals to monitor energy status. Some signals are peptide hormones (referred to here as "gut hormones") released from various parts of the body in response to a perceived energy status. These include those secreted by gastrointestinal endocrine cells such as glucose-dependent insulinotropic peptide (GIP). Such peptide hormones have short half-lives enabling a dynamic response to changing conditions. This allows their levels to be determined, analysed and correlated to food intake across a time period.

After a meal, gut hormones are secreted into the circulation in order to stimulate insulin secretion. GIP is one of these "incretin" hormones and blood levels are elevated in obesity and diabetes. GIP exerts various peripheral effects on adipose tissue and lipid metabolism, leading to increased lipid deposition in the post prandial state. GIP stimulates pro-inflammatory gene expression in adipose tissue and impairs insulin sensitivity. Blockade of GIP signalling has been shown to cause preferential oxidation of fat and to clear triacylglycerol deposits from liver and muscle. In obesity, hypoxia within adipose tissue can induce inflammation and there is a reported association between GIP and hypoxic signalling in adipose tissue inflammation. GIP receptor antagonism has been observed to reverse obesity, insulin resistance, and associated metabolic disturbances in mice.

Obesity is perceived to be the most significant health issue in companion animal nutrition with reports indicating that as many as 35-40% of cats and dogs are overweight/obese (Lund et. al., 2005; German, 2006). The accumulation of excess body fat has many detrimental effects on the health of animals including impaired glucose tolerance (insulin resistance), type 2 diabetes and chronic low grade tissue inflammation. Multiple factors are likely to be involved in weight gain and the development of obesity in cats and dogs, some of which may be considered to be intrinsic to the animal (e.g. genes, level of spontaneous physical activity), whilst others may be extrinsic (e.g. the amount and frequency of food provision). In companion animals, where food provision is almost exclusively determined by the carer/owner, it might be thought that the amount of food provided could be easily controlled to avoid weight gain. However, variability in the measuring of food portions has been shown to range from an 18% under-estimate to an 80% over-estimate in portion size, which over time could markedly affect body weight (German et. al., 2011).

Pet obesity is a major concern for companion animal health and nutrition. There is a need to control the body fat in companion animals. Many animal owners unintentionally over feed their animals. Companion animals do not control the amount of food they eat as their instinct is to eat as much as possible when food is available. For that reason, domestic animals tend to gain weight.

There is therefore a need to provide pet food products which aids companion animals to avoid the accumulation of body fat and therefore help to maintain a "healthy" body composition and controlling body weight of the companion animal, which will help to reduce the risk and/or prevent the development of health problems, such as insulin resistance and type 2 diabetes.

BRIEF DESCRIPTION

A method is provided, comprising the steps of: (a) feeding a companion animal, preferably a cat, a foodstuff comprising a protein to fat ratio of 1:0.27 to 1:0.63 on a gram:gram as fed or dry matter basis, and (b) measuring the level of glucose-dependent insulinotropic polypeptide (GIP) in a blood sample from the companion animal before and after feeding the foodstuff, wherein a reduction in GIP levels and/or maintaining low levels of GIP post-prandially is indicative of a foodstuff for use in preventing accumulation of and/or reducing body fat in a cat and therefore controlling the body weight of a companion animal.

The levels of GIP are measured at least once an hour or immediately before the foodstuff is fed to the cat and at least once between at least 30 minutes to 5 hours after the foodstuff has been fed to the cat.

The foodstuff may have a protein to fat ratio is about 1:0.33 to 1:0.55 on a gram:gram as fed or dry matter basis. The foodstuff may have a protein to fat ratio of about 1:0.45 on a gram:gram as fed or dry matter basis. The foodstuff may have a protein to fat ratio of about 1:0.37 on a gram:gram as fed or dry matter basis. The foodstuff, is preferably a nutritionally balanced pet foodstuff.

The post prandial concentration of GIP in the blood sample does not exceed 50 pg/ml, preferably the concentration of GIP in the blood sample is maintained and does not exceed 50 pg/ml for at least 30 minutes to 5 hours after the foodstuff is fed to the cat.

The method further comprises a step of formulating a foodstuff comprising a protein to fat ratio of 1:0.27 to 1:0.63 on a gram:gram as fed or dry matter basis that occurs prior to the step of feeding the cat the foodstuff.

BRIEF DESCRIPTION OF THE DRAWINGS

Further understanding of the embodiments described herein can be obtained via reference to the attached drawings, wherein.

DETAILED DESCRIPTION

Figure 1A:
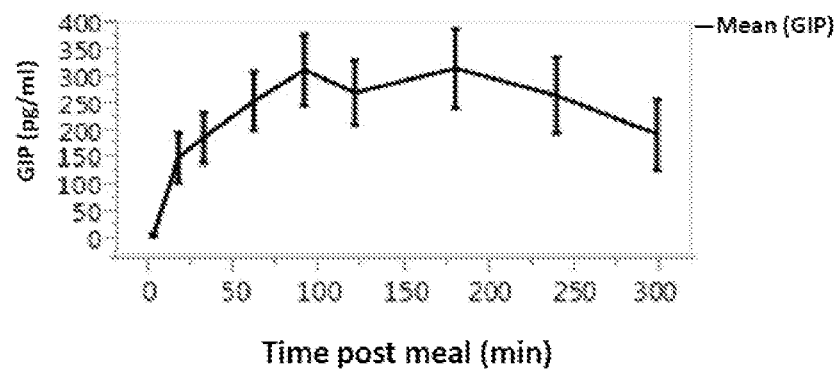
FIG. 1A is a graphical depiction of the GIP concentration vs time post meal for Diet 1 fed as described in Example 1.

In some embodiments, the pet foodstuff comprises a protein to fat ratio of 1:0.27 to 1:0.63 on a gram:gram as fed or dry matter basis and is for use in preventing accumulation of and/or reducing body fat in companion animals, preferably a cat. Preventing accumulation of and/or reducing the body fat of the companion animal is indicated by a reduction in the levels of glucose-dependent insulinotropic polypeptide (GIP) in blood sample of the companion animal.

The pet foodstuff for use in preventing accumulation of and/or reducing body fat in companion animals is a nutritionally balanced pet foodstuff. In particular, the foodstuff for use in preventing accumulation of and/or reducing body fat in companion animals has a protein to fat ratio is about 1:0.33 to 1:0.55.

In some embodiments, the method may prevent accumulation of and/or reducing the body fat of a companion animal, wherein the companion animal is fed a pet foodstuff comprising a protein to fat ratio of 1:0.27 to 1:0.63 on a gram:gram as fed or dry matter basis. Preventing accumulation of and/or reducing the body fat of the companion animal is indicated by a reduction in the levels of glucose-dependent insulinotropic polypeptide (GIP) in blood sample of the companion animal, preferably a cat.

The pet foodstuff used in the method for preventing accumulation of and/or reducing body fat in companion animals is a nutritionally balanced pet foodstuff. In particular, the foodstuff has a protein to fat ratio is about 1:0.33 to 1:0.55.

The pet foodstuff may further comprise one or more nutrients selected from group (a) and group (b), wherein the nutrients in group (a) are aspartic acid, serine, glutamic acid, glycine, alanine or proline and the nutrients in group (b) are myristic acid, palmitic acid, stearic acid, palmitoleic acid, oleic acid or linolenic acid. Preferably, the pet foodstuff comprises one nutrient from group (a) and one nutrient from group (b) and comprises a ratio of the group (a) nutrient to the group (b) nutrient of 1:0.006 to 1:4.5 on a gram:gram as fed or dry matter basis or wherein the pet foodstuff comprises two nutrients selected from group (a) and two nutrients selected from group (b) and comprises a ratio of group (a) nutrients to group (b) nutrients of 1:0.014 to 1:3.5 on a gram:gram as fed or dry matter basis or wherein the pet foodstuff comprises three nutrients selected from group (a) and three nutrients selected from group (b) and comprises a ratio of group (a) nutrients to group (b) nutrients of 1:0.025 to 1:2.5 on a gram:gram as fed or dry matter basis.

In some embodiments, a dietary regime for feeding a companion animal is provided that can assist in preventing accumulation of and/or reducing body fat, wherein the companion animal is fed a combination of at least two pet foodstuffs, wherein one pet foodstuff is wet or dry and comprises a ratio of protein:fat of 1:0.27 to 1:0.63 on a gram:gram as fed or dry matter basis and the second pet foodstuff is wet or dry and comprises a protein:fat of 1:0.27 to 1:0.63 on a gram:gram as fed or dry matter basis, wherein when combined the companion animal is fed an overall ratio of protein:fat of 1:0.27 to 1:0.63 on a gram:gram as fed or dry matter basis.

A method of determining the level of glucose-dependent insulinotropic polypeptide (GIP) before and after a meal in a companion animal is provided, wherein the meal is a pet foodstuff having a particular protein to fat ratio which is useful in reducing the levels of GIP and maintaining low levels of GIP post-prandially and having the beneficial effects as described herein.

The method comprises the following steps of: (a) feeding a companion animal a foodstuff comprising a protein to fat ratio of 1:0.27 to 1:0.63 on a gram:gram as fed or dry matter basis (i.e. the pet foodstuff as described herein), and (b) measuring the level of glucose-dependent insulinotropic polypeptide (GIP) in a blood sample from the companion animal before and after feeding the foodstuff, wherein a reduction in GIP levels and maintaining low levels of GIP (for example: not exceeding 50 pg/ml) postprandially is indicative of a foodstuff for use in preventing accumulation of and/or reducing body fat in a companion animal and therefore controlling the body weight of the companion animal.

Advantageously and beneficially, the method can be used as an indicator of whether the pet foodstuff is the factor providing the effect of reducing the levels of GIP and maintaining low levels of GIP in the companion animal and thus such pet foodstuff can be useful in providing the beneficial effects of preventing the accumulation of and/or reducing body fat in the companion animal and therefore useful in controlling the body weight of the companion animal.

The present invention relates, for all aspects, to any companion animal. In particular, the present invention relates to a companion animal such as a dog or a cat. In particular, the companion animal is a cat.

The pet foodstuff comprises a ratio of protein to fat of 1:0.27 to 1:0.63 on a gram:gram as fed or dry matter basis.

The foodstuff as described herein has been shown to reduce the levels of GIP post-prandially and is thus useful in preventing the accumulation of and/or reducing the body fat in companion animals and can have the overall effect of controlling the bodyweight of the companion animal. The inventors have surprisingly discovered that feeding a companion animal a pet food having the specific protein to fat ratio of 1:0.27 to 1:0.63 on a gram:gram as fed or dry matter basis lowers the GIP levels which includes the reduction of fat deposition, reduction of adipose tissue mass, reducing the adipose tissue inflammation and increasing fat oxidation therefore leading to a reduction in body fat and thus loss of weight and/or maintenance of weight in the companion animal and therefore the overall effect of controlling the bodyweight of the companion animal.

In humans, studies have shown that secretion of GIP is primarily induced by absorption of ingested fat and glucose. When fat and glucose are ingested, GIP is secreted and induces the secretion of insulin and fatty acid metabolism. In humans, lower levels of GIP have been associated with beneficial effects in obesity, diabetes and inflammation.

While it is acknowledged/recognised that current nutritional guidelines from scientific and industry bodies provide recommendations for dietary levels of protein and fat that are independent of each other, the present inventors have found that companion animals, in particular cats, fed a diet with the particular protein to fat ratio as described herein, in fact, reduce the levels of GIP in the companion animals.

In humans and rodents, GIP plays a key role in glucose homeostasis, lipid metabolism and may initiate tissue inflammation. Elevated circulating levels of GIP are associated with obesity and diabetes in humans and animal models. Increased GIP signalling in mice plays a significant role in adipose tissue inflammation (Chen et. al. 2015). In contrast, lower levels of GIP have been associated with beneficial effects in obesity, diabetes and inflammation. GIP receptor antagonist treatment in mice significantly decreases adipose tissue mass, adipocyte hypertrophy, and deposition of triglyceride in liver and muscle (McClean et al. 2007). GIP has been reported to cause preferential oxidation of fat and blockade of GIP signalling clears triacylglycerol deposits from liver and muscle (Irwin, and Flat 2009). It has been suggested that GIP may initiate adipose tissue inflammation (Gogebakan Ozlem, et al. 2015). Therefore, lower levels of GIP are beneficial in reducing adipose tissue inflammation, and other negative health effects associated with GIP.

The foodstuff as described herein is fed to a companion animal. It has been shown that feeding a pet foodstuff having the particular protein to fat ratio as described herein to a companion animal, in particular to a cat, reduces the post prandial GIP levels significantly and is able to maintain low GIP levels post-prandially (for example: not exceeding 50 pg/ml).

GIP plays a key role in glucose homeostasis and lipid metabolism in mammals. A reduction in GIP is known to be a beneficial effect in reducing or preventing obesity.

Obesity/diabetes in humans and animal models has been shown to be associated with elevated circulating GIP levels. Furthermore, GIP stimulates pro-inflammatory gene expression and impairs insulin sensitivity in cultured adipocytes. Thus, increased levels of GIP are clearly associated with negative effects on animal health and therefore a diet which minimises any increase in circulating levels of GIP would be beneficial in preventing or reducing the risk of accumulating excess body fat and therefore the associated adverse health effects. This is supported by evidence from studies in which GIP signalling was blocked that protected animals from obesity and by causing preferential oxidation of fat, cleared triacylglycerol deposits from liver and muscle, thereby restoring mechanisms for suppression of hepatic glucose output and improving insulin sensitivity.

The pet foodstuff as described herein is useful in reducing the body fat in companion animals. Reducing body fat includes the reduction of fat deposition, reduction of adipose tissue mass, reducing the adipose tissue inflammation and increasing fat oxidation. Thus the foodstuff used in the present invention comprising the particular protein to fat ratios as described is useful in preventing the accumulation of and/or reducing body fat in the companion animal and therefore useful in controlling the body weight of the companion animal.

The pet foodstuff describe herein is for use in reducing body fat in a companion animal and thus controlling bodyweight in a companion animal.

The pet foodstuff as described herein may comprise a ratio of protein to fat on a gram:gram as fed or dry matter basis that may range from 1:0.27 to 1:0.63, 1:0.28 to 1:0.62, 1:0.29 to 1:0.61, 1:0.30 to 1:0.60, 1:0.31 to 1:0.59, 1:0.32 to 1:0.58, 1:0.33 to 1:0.57, 1:0.34 to 1:0.56, 1:0.35 to 1:0.55, 1:0.36 to 1:0.54, 1:0.37 to 1:0.53, 1:0.38 to 1:0.52, 1:0.39 to 1:0.51, 1:0.40 to 1:0.50, 1:0.41 to 1:0.49, 1:0.42 to 1:0.48, 1:0.43 to 1:0.47, 1:0.44 to 1:0.46, and/or combinations thereof. The pet foodstuff may preferably comprise a protein to fat ratio ranging from 1:0.33 to 1:0.55 on a gram:gram as fed or a dry matter basis. The pet foodstuff may comprise a protein to fat ratio selected from 1:0.27, 1:0.28, 1:0.29, 1:0.30, 1:0.31, 1:0.32, 1:0.33, 1:0.34, 1:0.35, 1:0.36, 1:0.37, 1:0.38, 1:0.39, 1:0.40, 1:0.41, 1:0.42, 1:0.43, 1:0.44, 1:0.45, 1:0.46, 1:0.47, 1:0.48, 1:0.49, 1:0.50, 1:0.51, 1:0.52, 1:0.53, 1:0.54, 1:0.55, 1:0.56, 1:0.57, 1:0.58, 1:0.59, 1:0.60, 1:0.61, 1:0.62, or 1:0.63 gram:gram as fed or dry matter basis. The pet foodstuff preferably has a protein to fat ratio of about and/or approximately 1:0.45 on a gram:gram as fed or dry matter basis, most preferably the foodstuff has a protein to fat ratio of about and/or approximately 1:0.37 on a gram:gram as fed or dry matter basis.

The pet foodstuff as described herein can consist of a protein to fat ratio of about 1:0.33 to 1:0.55 on a gram:gram as fed or dry matter basis.

The pet foodstuff as described herein can preferably consist of a protein to fat ratio of about 1:0.45 on a gram:gram as fed or dry matter basis or most preferably of a protein to fat ratio of about 1:0.37 on a gram:gram as fed or dry matter basis.

The pet foodstuff as described herein can be a complete and nutritionally balanced pet food product.

The foodstuff can be any type which is consumed by the companion animal, such as dry product, semi moist product, wet food product or a liquid and includes any food supplement, snack or treat. This includes, standard food products including liquids, as well as pet food snacks (for example, snack bars, pet chew, crunchy treat, cereal bars, snacks, biscuits and sweet products).

Preferably, the pet foodstuff may be in the form of a dry foodstuff or a wet foodstuff. The foodstuff is, in particular, a nutritionally balanced food product and/or food supplement, for example a pet product and/or pet supplement.

The pet foodstuff is preferably a pet product. Such a product is a preferably sold as a product for feeding/administering to a companion animal, in particular to a cat or dog.

The content of protein and/or fat in the pet foodstuff can be any measure and/or weight percentage of the pet foodstuff desired, provided that the final ratio of protein to fat is of 1:0.27 to 1:0.63 gram:gram as fed basis or dry matter basis.

A typical dry pet foodstuff contains about 10-40% crude protein and about 5-40% fat, the remainder being carbohydrate, including dietary fibre and ash. A typical wet or moist product contains (on a dry matter basis) about 40% fat, 50% protein and the remainder being fibre and ash. The foodstuff may be a dry product (with approximately 5 to approximately 15% moisture), a semi-moist product (with approximately 15 to approximately 70% moisture) or a wet product (with approximately 70 to approximately 90% moisture).

As described above, the content of protein and/or fat in the pet foodstuff can be any measure and/or weight percentage of the pet foodstuff desired, provided that the final ratio of protein to fat is of 1:0.27 to 1:0.63 as fed basis or dry matter basis. For example, the pet foodstuff may be a wet foodstuff comprising a ratio of protein to fat on a gram:gram as fed or dry matter basis ranging from 1:0.27 to 1:0.63, wherein the content of protein is 10 g/100 g as fed basis then the content of fat can be 2.7 g/100 g to 6.3 g/100 as fed basis, most preferably 4.5 g/100 g as fed basis. For example, the pet foodstuff may be a dry pet foodstuff comprising a ratio of protein to fat on a gram:gram as fed or dry matter basis ranging from 1:0.27 to 1:0.63, wherein the content of protein is, 32 g/100 g on an as fed basis then the content of fat can be 8.6 g/100 g to 20.2 g/100 g on an as fed basis, most preferably about 14.4 g/100 g as fed basis.

The foodstuff is preferably a cooked product. It may incorporate meat or animal derived material (such as beef, chicken, turkey, lamb, fish, blood plasma, marrow bone etc. or one or more thereof). The product alternatively may be meat free (preferably including a meat substitute such as soya, maize gluten or a soya product) in order to provide a protein source. The foodstuff may contain additional protein sources such as soya protein concentrate, milk proteins, gluten etc. The foodstuff may also contain a fat source such as one or more of chicken fat, turkey fat, beef fat, duck fat, pork fat, lamb fat, fish oil, sunflower oil, vegetable oil, etc. The foodstuff may also contain a starch source such as one or more grains (e.g. wheat, corn, rice, oats, barley etc.), or may be starch free.

The foodstuff may be used alone or may be used in combination with a complete and balanced food which provides all the recommended vitamins and minerals for the companion animal in questions, for example, as described in National Research Council, 2006, Nutrient Requirements for Dogs and Cats, National Academy Press, Washington D.C. (ISBN:0-309-08628-0); or Association of American Feed Control Officials, Official Publication 2015.

The present description includes a method for preparing the pet foodstuffs as described herein. More specifically, the foodstuff described herein can be made according to any method known in the art.

The remaining components of the foodstuff are not essential to the invention and typical standard products can be included. The combined ingredients of the foodstuff according to the invention can provide all of the recommended vitamins and minerals for the particular animal in question (a complete and balanced food).

The pet foodstuff may include one or more nutrients selected from group (a) and group (b), as shown in Table 1, below, wherein the nutrients in group (a) are aspartic acid, serine, glutamic acid, glycine, alanine or proline and the nutrients in group (b) are myristic acid, palmitic acid, stearic acid, palmitoleic acid, oleic acid or linolenic acid.

TABLE 1

| Group A | Group B |
| --- | --- |
| Aspartic Acid | Myristic Acid |
| Serine | Palmitic Acid |
| Glutamic Acid | Stearic Acid |
| Glycine | Palmitoleic Acid |
| Alanine | Oleic Acid |
| Proline | Linolenic Acid |

The pet foodstuff may be any combination of nutrients from group (a) and group (b). The pet foodstuff may comprise aspartic acid, serine, glutamic acid, glycine, alanine or proline or any combination thereof and myristic acid, palmitic acid, stearic acid, palmitoleic acid, oleic acid or linolenic acid or any combination thereof.

The pet foodstuff may include one nutrient from group (a) (i.e., aspartic acid, serine, glutamic acid, glycine, alanine or proline) and one nutrient from group (b) (i.e., myristic acid, palmitic acid, stearic acid, palmitoleic acid, oleic acid or linolenic acid). In particular, when the pet foodstuff comprises one nutrient from each of group (a) and (b), the nutrients can be provided in a ratio of the group (a) nutrient to the group (b) nutrient of 1:0.006 to 1:4.5 on a gram:gram as fed or dry matter basis.

The pet foodstuff may include two nutrients from group (a) (i.e., aspartic acid, serine, glutamic acid, glycine, alanine or proline) and two nutrients from group (b) (i.e., myristic acid, palmitic acid, stearic acid, palmitoleic acid, oleic acid or linolenic acid). In particular, when the pet foodstuff comprises two nutrients from each of group (a) and (b), the nutrients can be provided in a ratio of group (a) nutrients to group (b) nutrients of 1:0.014 to 1:3.5 on a gram:gram as fed or dry matter basis.

The pet foodstuff may include three nutrients from group (a) (i.e., aspartic acid, serine, glutamic acid, glycine, alanine or proline) and three nutrients from group (b) (i.e., myristic acid, palmitic acid, stearic acid, palmitoleic acid, oleic acid or linolenic acid). In particular, when the pet foodstuff comprises one nutrient from each of group (a) and (b), the nutrients can be provided in a ratio of group (a) nutrients to group (b) nutrients of 1:0.025 to 1:2.5 on a gram:gram as fed or dry matter basis.

Blood samples are taken from the companion animal, at least once before a meal and one or more times after the meal. In particular, the blood samples can be taken one or more times after the meal at chosen intervals between at least 30 minutes to 5 hours after the meal (for example: every 15 minutes, every 30 minutes, every hour or at 15 minutes, 60 minutes, 120 minutes and 300 minutes following the end of the 20 minute meal). The meal referred herein is the pet foodstuff described having the particular protein to fat levels. Each blood sample taken from the companion animal is tested using standard assays, such as multispecies gut hormone Milliplex® assays, known in the art to determine the concentration levels of GIP. The timed intervals at which the samples are taken and the GIP concentrations measured are not to be strictly timed and are approximate.

The GIP concentration levels in the blood sample postprandially (i.e. after the companion animal has been fed the meal comprising the particular protein to fat ratio as described herein) are reduced when compared with the GIP measurement taken when the companion animal is fed a meal not having the particular protein to fat ratio as described herein. In particular, the GIP concentrations are significantly reduced when compared to the GIP measurements taken when the companion animal is fed the foodstuff having other protein to fat ratios other than that described herein.

It is specifically shown that GIP concentration levels in the blood sample postprandially (i.e. after the companion animal has been fed the foodstuff comprising the particular protein to fat ratio as described herein) do not exceed 50 pg/ml at least after 15 minutes following the end of the 20 minute meal, when measured using the multispecies gut hormone Milliplex® assay. In fact, the GIP concentration levels in the blood sample taken after the meal, when taken at any interval after the meal, or at least after 15 minutes following the end of the 20 minute meal, do not exceed above 50 pg/ml, when measured using the multispecies gut hormone Milliplex® assay. In particular, post prandial GIP concentrations are reduced and maintained at low levels for at least between 30 minutes to 5 hours, for example, post prandial GIP concentrations may be reduced/maintained for up to 30 minutes, 1 hour, 2 hours, 3 hours 4 hours or up to 5 hours. As used herein, the phrase "low levels of GIP" indicates a GIP concentration of less than or equal to 50 pg/ml.

Feeding a companion animal, in particular a cat, a pet foodstuff having the particular protein to fat ratio as described herein, reduces the post prandial GIP levels significantly and maintains low levels of GIP post-prandially. The pet foodstuff thus provides the companion animal with beneficial health effects such as preventing accumulation of and/or reducing body fat in the companion animal. As such, the foodstuff can aid the control of the bodyweight of the companion animal.

The method can include the step of preparing the pet foodstuffs used in the present invention. The foodstuff can be made according to any method known in the art.

The method can include a step of formulating the foodstuff comprising a protein to fat ratio of 1:0.27 to 1:0.63 on a gram:gram as fed or dry matter basis. Such a formulation occurs prior to the step of feeding the cat the foodstuff.

The pet foodstuff can also be provided in the form of a dietary regime, wherein the dietary regime comprises a wet foodstuff and dry foodstuff that enables the companion animal to achieve the particular protein to fat ratio as described herein through the consumption of both the wet and dry foodstuffs. Each of the wet and dry foodstuffs have a protein:fat ratio within the range 1:0.27 to 1:0.63 on a gram:gram as fed or dry matter basis.

The foodstuffs may be provided at the same time, to enable the animal to eat both types of foodstuff at the same meal to achieve the particular protein to fat ratio as described herein through the consumption of both the wet and dry foodstuffs. Alternatively, the wet food, for example, may be provided in the morning and the dry foodstuff may be provided as a separate meal in the afternoon or evening, meaning that in the course of 24 hours, the animal will achieve the particular protein:fat ratio as described herein.

The preferred protein:fat ratio may be achieved by the consumption of only the wet food or only the dry food or through any combination of each of wet and dry foodstuffs provided to the companion animal. With the foods provided in the dietary regime, the preferred protein:fat ratio (1:0.27 to 1:0.63 gram:gram as fed or dry matter basis) may be achieved by the companion animal self-selecting the required amounts of each of the wet and/or dry foodstuffs provided to it.

The levels of GIP can be measured at the beginning of the day, prior to the companion animal being fed and postprandially after the first meal of the day to obtain one measurement and then again prior to the companion animal being fed the second meal of the day and postprandially after the second meal of the day to obtain a second reading. Each of the wet and dry foodstuffs has a protein:fat ratio within the range 1:0.27 to 1:0.63 on a gram:gram as fed or dry matter basis, so the GIP levels will have decreased postprandially after both the first and second meal.

A kit is also provided and comprises a first package comprising a wet foodstuff and second package comprising a dry foodstuff for use in such a dietary regime or combinations thereof. Each of the wet and dry foodstuffs can have a protein:fat ratio within the range 1:0.27 to 1:0.63 on a gram:gram as fed or dry matter basis. Or, each of the wet and dry foodstuffs can individually have a protein:fat ratio below or above the range 1:0.27 to 1:0.63 on a gram:gram as fed or dry matter basis and when combined, can provide the protein:fat ratio within the range 1:0.27 to 1:0.63 on a gram:gram as fed or dry matter basis.

The invention also relates to methods of preventing the accumulation of and/or reducing the body fat of a companion animal by administering (or feeding) a companion animal with the pet foodstuff comprising the particular protein to fat ratios described (i.e. 1:0.27 to 1:0.63 on a gram:gram as fed or dry matter basis).

Preferred features of the invention apply mutatis mutandis.

Example

A study was performed in 19 cats aged between 1 and 2 years to investigate the impact of 5 diets on post prandial gut hormone levels. Five diets (labelled Diet 1, Diet 2, Diet 3, Diet 4 and Diet 5) were manufactured using the same raw materials but in different proportions to provide a range of protein to fat ratios. The compositions of diets 1-5, including the ratio of protein to fat in each diet are shown below in Table 2. The concentrations of certain amino acids and fatty acids present in diet 4 are shown below in Table 3.

All cats were fed in five consecutive phases of 14 days in a randomised crossover design with each cat being fed each of the 5 diets in turn. All cats were within 5% of ideal body weight at the start of the trial. For the first 13 days of each phase, cats were fed two meals per day in amounts to maintain a stable, healthy bodyweight. On day 14 of each phase, cats had blood samples taken at 5 time points (one prior to feeding as a baseline and then at 15, 60, 120, & 300 mins following the end of the 20 minute meal).

TABLE 2

Diet compositions and ratio of Protein:Fat

| Diet | Protein g/100 g | Carbohydrate g/100 g | Fat g/100 g | Energy kcal/100 g | P:F |
|---|---|---|---|---|---|
| 1 | 7.87 (low) | 2.55 (low) | 11.47 (high) | 132 | 1:1.46 |
| 2 | 7.47 (low) | 9.93 (medium) | 7.67 (medium) | 125 | 1:1.03 |
| 3 | 7.00 (low) | 12.68 (high) | 5.30 (medium) | 119 | 1:0.76 |
| 4 | 10.90 (high) | 2.71 (low) | 4.00 (medium) | 95 | 1:0.37 |
| 5 | 11.60 (high) | 9.87 (high) | 1.30 (low) | 92 | 1:0.11 |

TABLE 3

Concentrations of certain amino acids and fatty acids present in the diet associated with the beneficial effects on plasma GIP levels (diet 4).

| Nutrient | Concentration in diet (g/100 g as fed) |
|---|---|
| Aspartic Acid | 0.74 |
| Serine | 0.38 |
| Glutamic Acid | 1.14 |
| Glycine | 0.9 |
| Alanine | 0.6 |
| Proline | 0.55 |
| Myristic Acid | 0.03 |
| Palmitic Acid | 0.58 |
| Stearic Acid | 0.25 |
| Palmitoleic Acid | 0.13 |
| Oleic Acid | 0.90 |
| Linolenic Acid | 0.04 |

Measures:

Hormones—Blood samples were collected in chilled 0.5 ml EDTA treated collection tubes (Sarstedt, Leicester, UK) containing a 5 µl DPP-IV inhibitor (Cat# DPP4-010 Merck Millipore, Nottingham, UK) and 5 µl protease inhibitor cocktail (Cat# P2714 Sigma, Poole, UK) and rolled for 2 minutes to prevent clotting. Samples were kept on ice until the plasma was separated by centrifugation at 5100 rpm (2000×g) for 10 min at 4° C. in a 22R Microfuge (Beckman Coulter, High Wycombe, UK). The plasma was then harvested and snap frozen on dry ice, within 30 minutes of sampling. At the end of the sampling session the plasma was stored at −80° C. prior to analysis.

Plasma levels of total Glucose-dependent Insulinotropic Peptide (GIP), were measured using a Multispecies Gut Hormone Milliplex® assay validated for feline samples (Merck Millipore, Watford, UK). The units are measured in picograms per milliliter (pg/ml).

The Milliplex® assay is based on conventional sandwich assay technology. The antibody specific to each hormone is covalently coupled to Luminex® microspheres with each antibody coupled to a different microsphere uniquely labelled with a fluorescent dye. The microspheres can be discriminated by using the dual-laser based Luminex® xMAP technology (Luminex Corp, Austin, USA). This allows for the measurement of multiple hormones in a single assay using a limited volume of starting material. The assay was performed according to the manufacturer's protocol. Briefly, microspheres were incubated with standards, controls and samples (25 μl) in a 96-well microtiter filter plate overnight (18-19 hr) at 4° C. while shaking. After incubation, the plate was washed and the detection (streptavidin-labelled) antibody was added. After 30 minutes of incubation at room temperature, streptavidin-phycoerythrin was added for an additional 30 minute incubation. After washing, the concentration of the hormones of interest were analysed by detection of labelled antibody using the Luminex® 200 instrument (Luminex Corp, Austin, USA). All samples were tested in duplicate and the results reported as the mean of the duplicates.

TABLE 4

Mean concentration of GIP at each time point for each of Diets 1-5.

| Diet | Sample Time Post Meal | Mean(GIP) pg/ml | LowerCI[1] | UpperCI |
|---|---|---|---|---|
| 1 | 0 | 8.11 | 6.19 | 10.03 |
| 1 | 15 | 151.23 | 109.00 | 193.46 |
| 1 | 30 | 188.20 | 144.42 | 231.98 |
| 1 | 60 | 256.09 | 205.03 | 307.16 |
| 1 | 90 | 313.68 | 251.86 | 375.49 |
| 1 | 120 | 272.00 | 216.36 | 327.65 |
| 1 | 180 | 316.75 | 247.28 | 386.21 |
| 1 | 240 | 266.58 | 200.03 | 333.13 |
| 1 | 300 | 194.29 | 133.77 | 254.81 |
| 2 | 0 | 7.61 | 5.33 | 9.89 |
| 2 | 15 | 112.66 | 78.73 | 146.58 |
| 2 | 30 | 194.37 | 155.07 | 233.67 |
| 2 | 60 | 219.55 | 174.32 | 264.77 |
| 2 | 90 | 241.01 | 193.14 | 288.89 |
| 2 | 120 | 275.55 | 230.77 | 320.32 |
| 2 | 180 | 257.26 | 201.85 | 312.66 |
| 2 | 240 | 199.80 | 158.85 | 240.74 |
| 2 | 300 | 182.55 | 149.04 | 216.05 |
| 3 | 0 | 9.65 | 6.88 | 12.43 |
| 3 | 15 | 85.65 | 56.69 | 114.61 |
| 3 | 30 | 134.42 | 109.06 | 159.78 |
| 3 | 60 | 165.74 | 129.94 | 201.55 |
| 3 | 90 | 189.64 | 152.32 | 226.96 |
| 3 | 120 | 205.25 | 159.38 | 251.13 |
| 3 | 180 | 180.79 | 140.23 | 221.34 |
| 3 | 240 | 150.47 | 109.47 | 191.46 |
| 3 | 300 | 124.69 | 87.65 | 161.73 |
| 4 | 0 | 9.29 | 6.46 | 12.11 |
| 4 | 15 | 21.52 | 15.47 | 27.57 |
| 4 | 30 | 22.94 | 16.31 | 29.56 |
| 4 | 60 | 26.34 | 21.19 | 31.50 |
| 4 | 90 | 28.22 | 22.45 | 34.00 |
| 4 | 120 | 32.67 | 25.86 | 39.48 |
| 4 | 180 | 34.87 | 29.25 | 40.49 |
| 4 | 240 | 36.65 | 29.31 | 44.00 |
| 4 | 300 | 32.63 | 26.16 | 39.10 |
| 5 | 0 | 11.47 | 7.96 | 14.99 |
| 5 | 15 | 107.59 | 86.95 | 128.22 |
| 5 | 30 | 122.40 | 100.12 | 144.67 |
| 5 | 60 | 123.16 | 93.37 | 152.95 |
| 5 | 90 | 142.81 | 107.76 | 177.87 |
| 5 | 120 | 149.46 | 123.22 | 175.70 |
| 5 | 180 | 125.79 | 104.40 | 147.18 |
| 5 | 240 | 125.26 | 89.39 | 161.12 |
| 5 | 300 | 99.97 | 73.05 | 126.89 |

[1]"CI" = Confidence Interval

Results

Figure 1B:
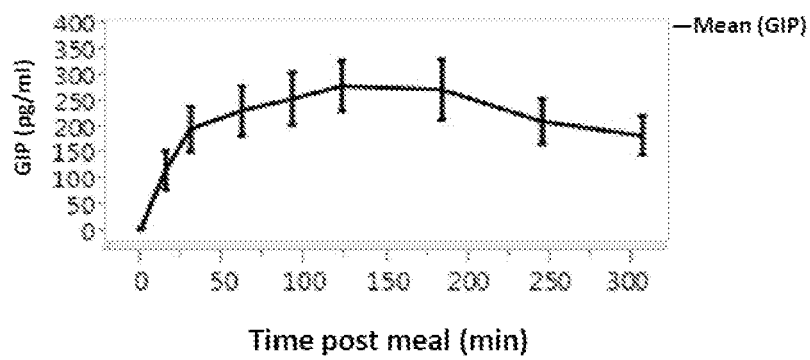
FIG. 1B is a graphical depiction of the GIP concentration vs time post meal for Diet 2 fed as described in Example 1.
Figure 1C:
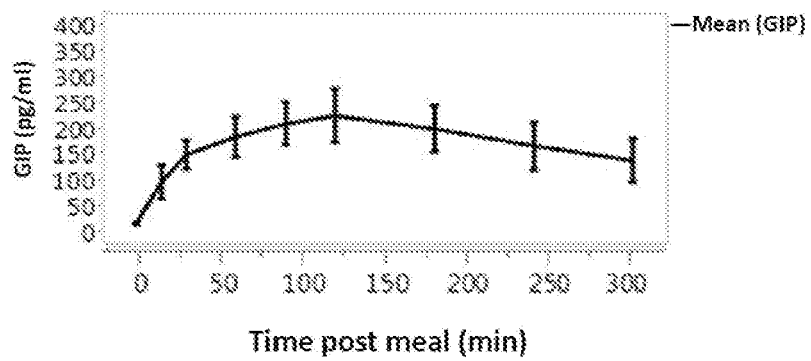
FIG. 1C is a graphical depiction of the GIP concentration vs time post meal for Diet 3 fed as described in Example 1.
Figure 1D:
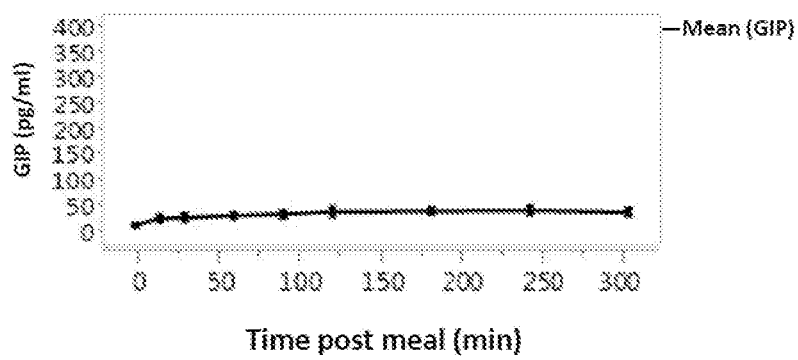
FIG. 1D is a graphical depiction of the GIP concentration vs time post meal for Diet 4 fed as described in Example 1.
Figure 1E:
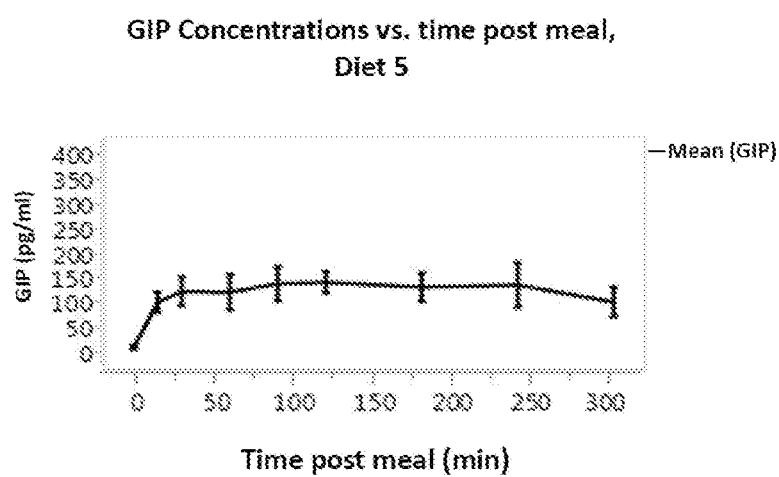
FIG. 1E is a graphical depiction of the GIP concentration vs time post meal for Diet 5 fed as described in Example 1.

The mean concentrations of GIP at each time point for each of Diets 1-5 are shown above in Table 4, and are graphically depicted in FIGS. 1A-1E. As shown, the plasma concentrations of GIP increased significantly after a meal and remained above baseline at all time points post meal for all diets offered. However, when the area under the curve ("AUC")—a reflection of the total amount of hormone released over time—of the GIP concentration response to each diet was investigated, the levels of GIP in the plasma were significantly lower when cats were offered diet 4 than when offered the other diets (FIGS. 1A-1E).

At all sample points after meals of Diets 1, 2, 3 and 5, the GIP concentrations were significantly higher than after meals of Diet 4. From 15 minutes post meal until 240 minutes post meal, levels of GIP after Diets 1, 2, 3 and 5, were significantly higher than after meals of Diet 4. (FIGS. 1A-1E). From thirty minutes following a meal, plasma GIP concentrations were significantly lower for cats that consumed diet 4 than cats that consumed the other diets (FIGS. 1A-1E). The results of this study show that feeding a diet with a protein:fat ratio of 1:0.37 (diet 4) resulted in minimal increases in plasma GIP concentration and therefore would be beneficial in preventing accumulation of adipose tissue (i.e., reducing body fat), reducing adipose tissue inflammation, preferentially increasing fat oxidation to clear tissue accumulation of triglycerides and thus reducing insulin resistance.

The invention claimed is:

1. A method of screening a cat food, comprising:
   (a) preparing a foodstuff expected to provide a stabilized GIP level upon ingestion by a cat, the GIP-stabilizing foodstuff consisting essentially of aspartic acid, serine, glutamic acid, glycine, alanine, proline, of myristic acid, palmitic acid, stearic acid, palmitoleic acid, oleic acid and linolenic acid, the foodstuff further comprising a protein to fat ratio of 1:0.27 to 1:0.63 on a gram:gram as fed or dry matter basis,
   (b) feeding the cat solely the foodstuff for at least 14 days,
   (c) measuring the level of glucose-dependent insulinotropic polypeptide (GIP) in a blood sample from the cat before and after feeding the foodstuff, and
   (d) evaluating the measured GIP levels to determine whether the foodstuff is effective to stabilize the GIP level of a cat,
   wherein a measured GIP level of 50 pg/ml or less postprandially indicates a foodstuff effective to stabilize the GIP level of a cat.

2. The method of claim 1, wherein the levels of GIP are measured at least once before the foodstuff is fed to the cat and at least once between at least 30 minutes to 5 hours after the foodstuff has been fed to the cat.

3. The method of claim 1, wherein the foodstuff has a protein to fat ratio of about 1:0.33 to 1:0.55 on a gram:gram as fed or dry matter basis.

4. The method of claim 1, wherein the foodstuff has a protein to fat ratio of about 1:0.45 on a gram:gram as fed or dry matter basis.

5. The method of claim 1, wherein the foodstuff has a protein to fat ratio of about 1:0.37 on a gram:gram as fed or dry matter basis.

6. The method of claim 1, wherein the post prandial concentration of GIP in the blood sample does not exceed 50 pg/ml.

7. The method of claim 1, wherein the post prandial concentration of GIP in the blood sample is maintained and does not exceed 50 pg/ml for at least 30 minutes to 5 hours after the foodstuff is fed to the cat.

* * * * *